(12) United States Patent
Doherty et al.

(10) Patent No.: US 8,152,071 B2
(45) Date of Patent: Apr. 10, 2012

(54) MULTI-PURPOSE PORTABLE COMPUTER WITH INTEGRATED DEVICES

(75) Inventors: John Doherty, Austin, TX (US); Mike Collins, Austin, TX (US)

(73) Assignee: Motion Computing, Inc., Austin, TX (US)

( * ) Notice: Subject to any disclaimer, the term of this patent is extended or adjusted under 35 U.S.C. 154(b) by 813 days.

(21) Appl. No.: 12/028,411

(22) Filed: Feb. 8, 2008

(65) Prior Publication Data

US 2009/0200378 A1    Aug. 13, 2009

(51) Int. Cl.
*G06K 7/10*    (2006.01)
(52) U.S. Cl. ................... 235/472.01; 235/454
(58) Field of Classification Search .......... 235/454, 235/472.01
See application file for complete search history.

(56) References Cited

U.S. PATENT DOCUMENTS

| | | |
|---|---|---|
| 5,086,509 A | 2/1992 | Inubushi et al. |
| 5,424,913 A | 6/1995 | Swindler |
| 5,430,609 A | 7/1995 | Kikinis |
| 5,583,742 A | 12/1996 | Noda et al. |
| 5,625,535 A | 4/1997 | Hulsebosch et al. |
| 5,656,876 A | 8/1997 | Radley et al. |
| 5,752,011 A | 5/1998 | Thomas et al. |
| 5,835,298 A | 11/1998 | Edgerton et al. |
| 5,907,471 A | 5/1999 | Patel et al. |
| 5,931,297 A | 8/1999 | Weill et al. |
| 5,969,940 A | 10/1999 | Sano et al. |
| 5,974,557 A | 10/1999 | Thomas et al. |
| 6,119,179 A | 9/2000 | Whitridge et al. |
| 6,122,167 A | 9/2000 | Smith et al. |
| 6,138,826 A | 10/2000 | Kanamori et al. |
| 6,145,280 A | 11/2000 | Daroux et al. |
| 6,216,235 B1 | 4/2001 | Thomas et al. |
| 6,233,464 B1 | 5/2001 | Chmaytelli |
| 6,262,886 B1 | 7/2001 | DiFonzo et al. |
| 6,267,790 B1 | 7/2001 | Daroux et al. |
| 6,319,199 B1 | 11/2001 | Sheehan et al. |
| 6,336,080 B1 | 1/2002 | Atkinson |
| 6,487,668 B2 | 11/2002 | Thomas et al. |
| 6,567,120 B1 | 5/2003 | Hamamura et al. |
| 6,657,859 B1 | 12/2003 | Karr |
| 6,659,274 B2 | 12/2003 | Enners |
| 6,684,089 B1 | 1/2004 | Lee |

(Continued)

FOREIGN PATENT DOCUMENTS

JP    11-143585    5/1995

OTHER PUBLICATIONS

Office Action mailed Feb. 3, 2010 for U.S. Appl. No. 12/028,458.

(Continued)

*Primary Examiner* — Daniel Hess
(74) *Attorney, Agent, or Firm* — Charles D. Huston; Daffer McDaniel, LLP (57) ABSTRACT

A portable computer having multiple modes of connectivity is disclosed. The portable computer may be configured to communicate using several wireless transmission protocols, including WWAN, WiFi, and Bluetooth. The portable computer may also receive input from multiple devices, including a bar code scanner, camera, RFID reader, fingerprint reader, digitizer, and an audio subsystem. The portable computer may also contain an accelerometer, and may be configurable to automatically park its hard drive disk when acceleration of a predetermined magnitude is detected.

16 Claims, 7 Drawing Sheets

U.S. PATENT DOCUMENTS

| | | |
|---|---|---|
| 6,746,638 B1 | 6/2004 | Zadesky et al. |
| 6,789,611 B1 | 9/2004 | Li |
| 6,803,144 B2 | 10/2004 | Hovi et al. |
| 6,809,698 B2 | 10/2004 | Tsai et al. |
| 6,888,332 B2 | 5/2005 | Matsushita |
| 6,927,978 B2 | 8/2005 | Arai et al. |
| 7,013,558 B2 | 3/2006 | Bachman |
| 7,016,181 B2 | 3/2006 | Ito et al. |
| 7,145,769 B2 | 12/2006 | Chen |
| 7,155,202 B2 | 12/2006 | Helal |
| 7,184,260 B2 | 2/2007 | Itoh et al. |
| 7,209,035 B2 | 4/2007 | Tabankin et al. |
| 7,221,957 B2 | 5/2007 | Takamura et al. |
| 7,245,482 B2 | 7/2007 | Kim |
| 7,273,089 B2 | 9/2007 | Hata et al. |
| 7,278,579 B2 | 10/2007 | Loffredo et al. |
| 7,286,894 B1 | 10/2007 | Grant et al. |
| 7,312,992 B2 | 12/2007 | Jory et al. |
| 7,325,846 B2 | 2/2008 | Smith et al. |
| 7,336,489 B1 | 2/2008 | Chen et al. |
| 7,382,607 B2 | 6/2008 | Skillman |
| 7,388,161 B2 | 6/2008 | Hsieh et al. |
| 7,405,930 B2 | 7/2008 | Hongo et al. |
| 7,428,143 B1 | 9/2008 | Jones et al. |
| 7,446,753 B2 | 11/2008 | Fitch et al. |
| 7,456,751 B2 | 11/2008 | Arai et al. |
| 7,495,895 B2 | 2/2009 | Carnevali |
| 7,499,232 B2 * | 3/2009 | Hodge et al. .................. 360/60 |
| 7,514,765 B2 | 4/2009 | Huang et al. |
| 7,674,540 B2 | 3/2010 | Adams et al. |
| 2002/0053421 A1 | 5/2002 | Hisano et al. |
| 2002/0067520 A1 | 6/2002 | Brown et al. |
| 2002/0085342 A1 | 7/2002 | Chen et al. |
| 2003/0184958 A1 | 10/2003 | Kao |
| 2003/0236102 A1 | 12/2003 | Kawai et al. |
| 2004/0107372 A1 | 6/2004 | Morisawa |
| 2004/0201602 A1 | 10/2004 | Mody et al. |
| 2004/0204041 A1 | 10/2004 | Fillebrown et al. |
| 2005/0040224 A1 | 2/2005 | Brinton et al. |
| 2005/0128693 A1 | 6/2005 | Itoh |
| 2005/0130721 A1 | 6/2005 | Gartrell |
| 2005/0139498 A1 | 6/2005 | Goros |
| 2005/0276018 A1 | 12/2005 | Moore et al. |
| 2005/0280984 A1 | 12/2005 | Huana et al. |
| 2006/0044288 A1 | 3/2006 | Nakamura et al. |
| 2006/0057458 A1 | 3/2006 | O'Dea et al. |
| 2006/0125782 A1 * | 6/2006 | Orchard et al. ................ 345/156 |
| 2006/0139807 A1 * | 6/2006 | Shimotono et al. ........... 360/137 |
| 2007/0085015 A1 | 4/2007 | Castleberry |
| 2007/0139873 A1 | 6/2007 | Thomas et al. |
| 2007/0174152 A1 | 7/2007 | Bjornberg et al. |
| 2007/0188306 A1 | 8/2007 | Tethrake et al. |
| 2007/0282208 A1 | 12/2007 | Jacobs et al. |
| 2008/0019093 A1 | 1/2008 | Hongo |
| 2008/0081679 A1 | 4/2008 | Kawasaki et al. |
| 2008/0094786 A1 | 4/2008 | Liou et al. |
| 2008/0123287 A1 | 5/2008 | Rossell et al. |
| 2008/0144270 A1 * | 6/2008 | Dal Porto et al. ............. 361/684 |
| 2008/0227507 A1 | 9/2008 | Joo |
| 2010/0008028 A1 | 1/2010 | Richardson et al. |

OTHER PUBLICATIONS

Office Action mailed Jun. 16, 2009 for U.S. Appl. No. 12/028,362.

Doherty et al., U.S. Appl. No. 12/028,362 entitled "Portable Computer with Thermal Control and Power Source Shield," filed Feb. 8, 2008.

Doherty et al., U.S. Appl. No. 12/028,458 entitled "Ergonomic Solvent Resistant Portable Computer," filed Feb. 8, 2008.

Final Office Action Mailed Sep. 4, 2009 for U.S. Appl. No. 12/028,362.

International Search Report & Written Opinion, PCT/US2009/032845, mailed Sep. 18, 2009.

Office Action mailed Jun. 29, 2010 for U.S. Patent Application No. 12/634,340.

Final Office Action mailed Oct. 25, 2010 for U.S. Appl. No. 12/634,340.

* cited by examiner

MULTI-PURPOSE PORTABLE COMPUTER WITH INTEGRATED DEVICES

BACKGROUND OF THE INVENTION

1. Field of the Invention

The invention relates to the field of portable computing devices, and more particularly, to a portable computing device that can be used to gather data in a number of environments, such as healthcare, warehouse, and shipping environments. The portable computer has a robust group of integrated input and output devices for extensive data capture, and is fabricated to be easily cleanable and resistant to contamination.

2. Description of the Related Art

Portable personal computers (PCs), including tablet PCs, laptop computers, and personal digital assistants (PDAs), allow computer users to utilize many of the functions of a personal computer while facilitating freedom of movement about a workplace. One type of portable computer, the tablet PC, can offer a very high level of mobility and flexibility to the user. These types of portable computers are well suited for use in the medical profession, where a doctor or nurse can use the portable computer in place of a pen and paper. Because portable computers allow users to easily update files electronically while also recording data on a single device and moving from point to point, they are potentially very useful in manufacturing and shipping environments where they may be used to track inventory, record inspection data and manage work flow.

By comparison to a desktop computer, portable computers are compact, lightweight, and easy to carry. However, portable computer designs may be limited by a tradeoff between compactness and robustness. In other words, portable computers can be made small and lightweight by reducing the amount of material that is devoted to strengthening and cushioning the device. Similarly, adding design elements that strengthen a device or make it more impact resistant usually entails making the device heavier and/or larger. Another design consideration, processing capability, may also inhibit the utility of portable computers in particularly moist or dirty environments. For instance, increasing the processing power of a computer generally equates to increasing the amount of heat the device will produce. Such heat must be dissipated, either through an active cooling system or through the body of the device. Excessive heat dissipation through the body of the device may cause the exterior of the device to become so hot that it may burn a user or at least cause them discomfort. While an active cooling system, such as a fan, cools the computer in a more ergonomic fashion, an active cooling system generally requires recesses and an airflow path through the computer. The airflow openings of a typical active cooling system may make the portable computer susceptible to contamination by dust, dirt, and germs. Similarly, because the contamination may occur in sensitive areas of the PC that are difficult and impractical to access and clean, it may be difficult to disinfect or clean the PC without damaging it.

SUMMARY OF THE INVENTION

The problems outlined above are in large part solved by a portable computer that comprises at least two radios and at least two image capture devices. The first radio is configured to transmit and receive data at a first time and a second radio is configured to transmit and receive data at a second time. At a third time, a first image capture device is configured to gather data and a second image capture device is configured to gather data at a fourth time.

A method for capturing data is also disclosed. The method comprises receiving data by a portable computer that has two or more radios during a first time via a first radio and during a second time via a second radio; and receiving data by a portable computer having two or more image capture devices during a third time via a first image capture device and during a fourth time via a second image capture device.

Further, an electronic device is disclosed that may be optimized to gather, store, and transmit data in a clinical environment. The electronic device comprises an accelerometer, a controller, a memory, at least two antennas internal to the electronic device, and at least two image capture devices internal to the electronic device.

BRIEF DESCRIPTION OF THE DRAWINGS

Other objects and advantages of the invention will become apparent upon reading the following detailed description and upon reference to the accompanying drawings in which:

FIG. 1b is a top perspective view of the portable computer of FIG. 1a;

FIG. 1c is a right side perspective view of the portable computer of FIG. 1a;

FIG. 2 is a rear perspective view of the portable computer of FIG. 1a;

FIG. 3 is a perspective view of an exemplary use of the portable computer of FIG. 1a;

FIG. 4 is a perspective view of another exemplary use of the portable computer of FIG. 1a;

FIG. 5 is a perspective view of another exemplary use of the portable computer of FIG. 1a;

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but are instead intended to cover all modifications, equivalents and alternatives falling within the spirit and scope of the present invention as defined by the appended claims.

DETAILED DESCRIPTION OF PREFERRED EMBODIMENTS

In response to the aforementioned limitations of portable computers, a tablet style portable computer is disclosed that is optimized to function in typically adverse environments, such as healthcare, manufacturing, and shipping environments. These environments are unique because they subject the computer to a disproportionately high amount of contaminants by comparison to a typical office environment. Healthcare environments may expose the computer to hazardous airborne contaminants, such as germs and bacteria. Similarly, manufacturing and shipping environments may expose a computer to liquids, dust and other particulate contaminants that can penetrate into a computer and degrade performance or cause the computer to malfunction. Because of the increased possibility of contamination and accumulation of dust, computers used in these fields must be designed to prevent contamination of interior surfaces while incorporating an exterior design that is easy to clean. These contaminant-heavy fields also require workers to be very mobile, so any computer focused for such use should be resistant to impact as well as easily carried and maneuvered by the user.

In a preferred embodiment, the portable computer integrates traditional computer features with data capture technologies, handwriting recognition, and speech recognition. The portable computer minimizes the number of ports and connectors, creating a semi-sealed device that is easier to clean and disinfect. It may include several built-in data capture technologies, such as a bar code scanner, radio frequency identification (RFID) reader, finger print scanner, and camera, thereby eliminating the need for bulky external devices. The design of the portable computer may provide a balance between performance and portability that is optimized for use in the healthcare, manufacturing, and shipping environments. The portable computer may include one or more processors that enable wireless communication, one or more types of memory, a display, integrated Wi-Fi (802.11a/b/g), WWAN (wireless broadband) networking, Bluetooth, a fingerprint reader, a camera, a barcode reader, a passive RFID reader, and a high-frequency passive RFID tag. Here, WWAN refers to a wireless broadband protocol. Typically, WWAN protocols use cellular network technologies such as WIMAX, UMTS, GPRS, CDMA2000, or a similar protocol to transfer data. WWAN technologies are typically offered regionally, nationwide, or even globally by wireless service providers, and as such, do not require a nearby access point to connect a computer to a network.

Figure 1A:
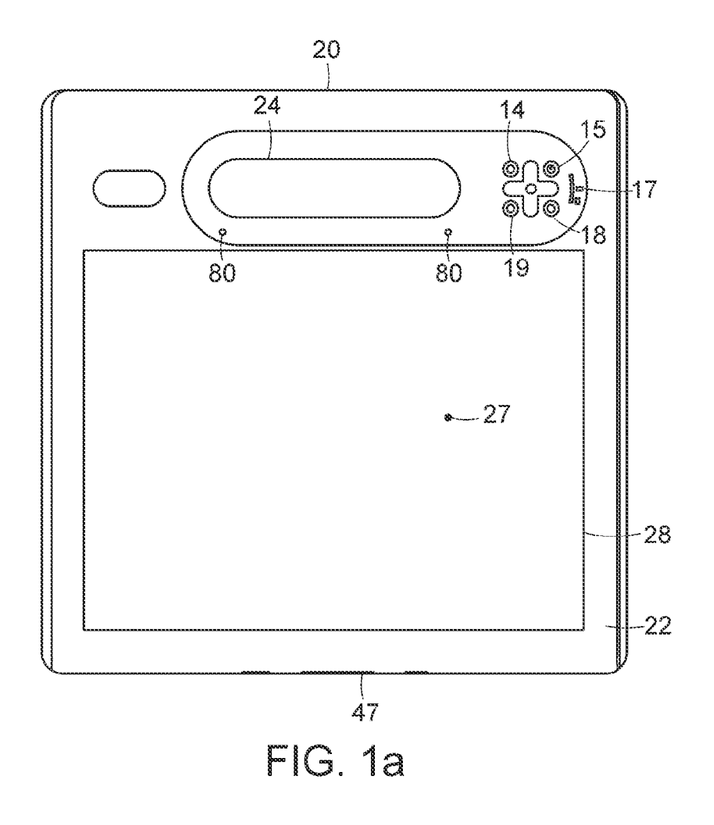
FIG. 1a is a front perspective view of a portable computer that is optimized for use in a clinical environment.

Turning to the drawings, FIG. 1a is a front view showing an embodiment of a portable computer (PC) 20 that is optimized for use in the healthcare industry. The body of the PC is formed to include handle 24 and comprises a magnesium alloy frame and exterior surface 22 comprising of plastic parts overmolded with elastomer. The soft elastomer overmolding may be achieved by first molding a plastic cover to mate with the metal frame of the computer, inserting the plastic cover into an elastomer mold to form an elastomeric layer on the plastic, and subsequently installing the plastic cover onto the metal frame of the computer. However, it is noted that similar processes for achieving the soft elastomer outer layer or overmolding may be substituted. Overmolded exterior 22 serves several important functions. The elastomer's softness relative to a typical metal frame provides the PC user a better tactile feel, and may help to absorb impact and prevent damage if the portable computer is dropped or otherwise subject to impact. Further, the elastomer exterior 22 has a low thermal conductivity that will insulate a user from heat produced by the PC and conducted by the magnesium alloy frame, and can be molded to conform to the contours of the computer. An additional benefit of using a particular elastomer and substrate plastic (for example, Valox), is that it is resistant to solvents that may be used to clean and disinfect the computer. Here, Valox is a family of thermoplastic polyester resins that are semi-crystalline materials, and based on polybutylene terephthalate (PBT) and/or polyethylene terephthalate (PET) polymers. For effective cleaning, a polymer such as Valox molded to form the exterior surfaces of the computer not covered by a chemically resistant elastomer may endure exposure to a variety of solvents used for cleaning and disinfecting without sustaining damage. Such solvents may include antimicrobial solvents, window cleaner, and EPA approved low-level disinfectants, such as formaldehyde, phenolic compounds, and iodophoric compounds.

FIG. 1a also shows a 10.4 inch liquid crystal display (LCD) 28 that allows information to be viewed easily without the need for excessive scrolling, and a set of thumb controls. The thumb controls may be used to operate a variety of devices that may be integrated into the PC, such as a digital camera and fingerprint scanner. More particularly, this set of thumb controls or "buttons" may comprise a function button 14 that activates secondary functions for the other buttons; a "Dashboard" button 15 that may call a control panel type graphical user interface; a directional pad 16 that has functionality that is equivalent to the arrows on a keyboard; a customizable "A" button 18 that can be assigned a function by the user; and a "B" button 19 that can also be assigned a function by the user. The assignable functions may include starting a program, running a command, or entering a key combination. A user may assign a program, command, or key combination by first opening an associated utility panel application; selecting the button they wish to assign a program, command, or key combination to; subsequently selecting an action to associate with the button; and saving the configuration.

Directional pad 16, which has up, down, and left/right arrows, may automatically orient itself to match the display orientation so that the up arrow will always point toward the top of display 28. For example, the button that functions as the "up" in a landscape orientation becomes the "left" in a portrait orientation. As such, a user may easily change the screen orientation to fit their current task. For instance, the portrait orientation may be better suited for filling out forms or reading an e-book, while the landscape orientation may be more ideal for Web browsing or sketching. Next to the thumb controls are status lights 17 that may indicate that status of a wireless communications radio, a Bluetooth radio, and the battery. More particularly, status lights 17 may comprise a number of LED (or similar) indicators that indicate the status of a number of attributes of the computer. For instance, status lights 17 may indicate whether the Wi-Fi (802.11a/b/g) adapter is enabled; whether the battery is charging; whether the battery is charged; whether the battery has only ten percent of its charge remaining; whether the battery has only five percent of its charge remaining; whether the Bluetooth adapter is enabled; and the function of the stylus.

FIG. 1a also shows microphones 80 that may record sounds and enable a user to operate the computer by issuing voice commands via voice recognition software. In order for the microphone to function optimally, it may be necessary for the user to calibrate the microphone's angle of acceptance. Generally, the angle of acceptance defines how the built-in microphones detect sounds. Because the computer contains multiple microphones, it is able to determine the angle, relative to the microphones, from which a sound originates. When a computer is operated with a speech recognition program, it may be desirable for the computer to only accept commands issued from directly in front of it. As such, the microphone may be configured to ignore all sounds outside of a specified angle of acceptance, and a user may adjust the angle of acceptance to optimize the microphones for dictation and voice command input. A narrow angle setting may be invoked to optimize the computer for dictation, voice over IP, or noisy environments. The narrow angle setting configures the microphones to detect sound on a narrow angle near the bottom center of the display. A medium angle setting may be optimal for use by a small group, at a conference table, or in a quiet environment. The microphones may also have a skew setting that corresponds to the direction from which the computer expects to receive sounds. The computer may have at least two sound input modes: dictation mode and voice command mode. In dictation mode, the computer listens to a user's voice and converts their words to text. In voice command mode, the computer listens for specific words that correspond to a list of available voice commands that may be used to switch between programs, save documents, copy text, and paste text.

Many of the features of PC 20 are geared for use in a clinical environment. However, it will be apparent to one of skill in the art that these features will render the device useful in a number of environments. In particular, handle 24 makes the computer easy to grip, a robust design helps to protect the computer if it is dropped, and a stylus input device enables workers to input data without needing a keyboard or mouse. The device may also include various integrated data capture devices, such as a fingerprint scanner, bar code scanner, and RFID reader to authenticate the identity of users, patients and medication. Other integrated devices, such as a camera for documenting symptoms and injuries may also prove useful. The computer may also have multiple 802.11a/b/g (Wi-Fi), wireless broadband (WWAN), and Bluetooth radios that allow it to wirelessly interface with other devices and networks with similar connectivity. In one embodiment, the computer may have seven or more radio devices: primary and secondary WiFi, a tertiary MIMO (802.11n), primary and secondary wireless broadband (WWAN), Bluetooth (WPAN), and a RFID reader. This heightened level of connectivity may help a user gather data without taking notes or subsequently transcribing recorded data, and may also allow data to be instantaneously uploaded to a network to update files stored in a central location. PC 20 may also help to save time by equipping workers with a small dedicated computer so they will not have to find and share a common desktop PC when their job requires them to use a computer.

Figure 1B:
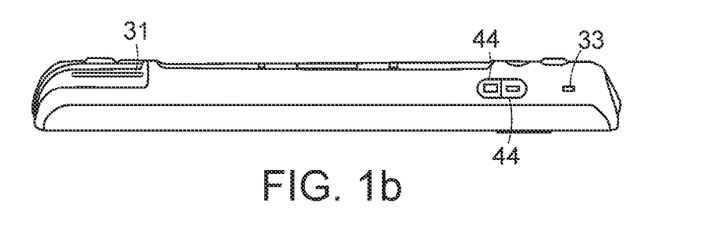
Figure 1C:
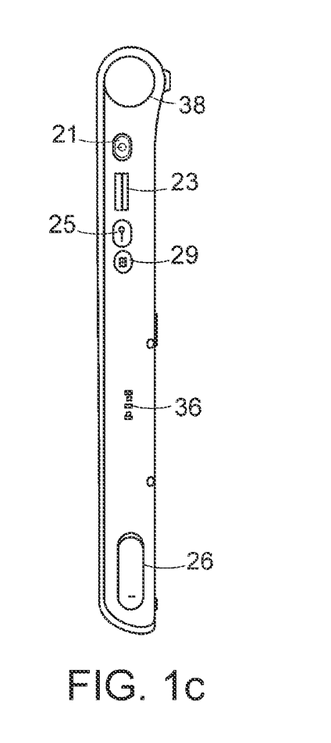

The computer may also comprise many integrated devices, some of which are illustrated in FIGS. 1b and 1c. FIG. 1c shows the right-hand side of the portable computer of FIG. 1a. Here, the computer has a sealable power adapter port 26 and a Windows™ security button 25 that has functionality equivalent to tapping "Ctrl-Alt-Delete" on a typical PC. This side of the computer also has power button 21, bar code scanner window 38, finger print reader 23, and RFID reader 36. FIG. 1b, which shows the top of the computer of FIG. 1a, illustrates removable fan cover 31, thumb control/button 44 that controls the RFID reader, RFID status light 33, and bar code scanner control/button 48. Returning the FIG. 1c, this side of the computer may also have camera button 29 that may trigger an integrated camera. An integrated 13.56 MHz RFID reader may be used to retrieve information from RFID tags that use radio frequency (RF) transmissions to identify a product, animal, or person. This may be particularly advantageous because RFID does not require direct contact or line-of-sight scanning, and can be scanned through many materials, including clothing and water. An RFID tag can also store much more data than a typical bar code, and sophisticated RFID tags can both transmit and record data. RFID can be used for asset tracking, identification, process control, health care, and pharmaceutical applications. The RFID reader may support multiple RFID formats, including ISO/IEC 14443A/B, ISO/IEC 15693, and ISO/IEC 18000-3. A bar code scanner may also be integrated into the computer so that users may retrieve bar code information for asset tracking, identification, process control, health care, and pharmaceutical applications.

The RFID reader may be a near field (approximately two inches or less) RF transceiving device that transmits an activation signal to an RFID tag and then receives a response signal transmitted from an active RFID tag. In another embodiment, the RFID reader may only receive data from a RFID tag where passive RFID tags are used. Passive RFID tags differ from active RFID tags in that they transmit constantly at a low power level, and function without the need for an activation signal. The transceiver of the RFID reader may be positioned along the right hand side of the device shown in FIG. 1c so that a user will be able to "scan" an RFID tag in much the same way they would use the bar code scanner to read a bar code by placing the RFID tag within close proximity of the RFID antenna.

In order for the computer to record bar code information, the data stored in the bar code must first be captured and decoded. Accordingly, the computer may contain a bar code scanner that captures the bar code data and sends it to a decoder. Once received by the decoder, the decoder can translate the bars and spaces that make up the bar code and translate the information to a conventional data format. Several types of bar code scanners are known in the art: pen type readers, laser bar code readers, CCD (charge couple devices) scanners, and camera based readers. Generally a bar code scanner functions by emitting light across the bar code and measuring the amount of light that is reflected back. The scanner may then convert the sensed reflected light into an electrical signal that is communicated to the computer. Here, a laser scanner may present the greatest degree of utility. Laser scanners may work from as far away from the bar code as 24 inches, and some long range scanners may function from much greater distances.

In some embodiments, the light used to read the bar code, camera light 37, or even an independently controlled light source, may be selectively switched on and off by a user so that the computer can also operate as a flashlight. This functionality may be user initiated through control of thumb controls/buttons, and may also be initiated through the computer's control panel utility. The flashlight capability may be particularly desirable to a healthcare worker who wishes to perform their duties while taking care to not disturb their patient.

The portable computer may include a 10.4" XGA TFT LCD display with a protective layer that offers a firm writing surface and minimizes glare, and a digitizer panel that enables handwritten data entry via the stylus. The computer may also have a variety of security features, and may employ a software utility to manage passwords and other security settings. The utility may be used to capture a user's fingerprint, so that they can subsequently use the fingerprint scanner to authenticate their identity in place of a password. The computer may also employ other security features and passwords, and may also allow for the BIOS and hard drive disk to be password protected. The BIOS password, and may be used to secure the basic input/output system of the computer, and the hard drive disk password may be used to protect the computer and hard disk drive (HDD). If a HDD password is implemented, the computer cannot be started without the password, and data on the disk drive may not be accessed, even if it is removed and attached to a different computer. As an additional security measure, the RFID reader may also be used to authenticate a user by scanning a user's identification badge if it contains an RFID tag. The device itself may also have an integrated RFID tag that can be used for identification and asset tracking. The benefits of some security measure may be two-fold because they not only serve to protect sensitive information but also to provide a faster and easier way for a user to authenticate their identity when logging onto a computer. For instance, in some embodiments, a user may log on to their computer by simply scanning their fingerprint rather than taking the time to type a password.

Figure 2:
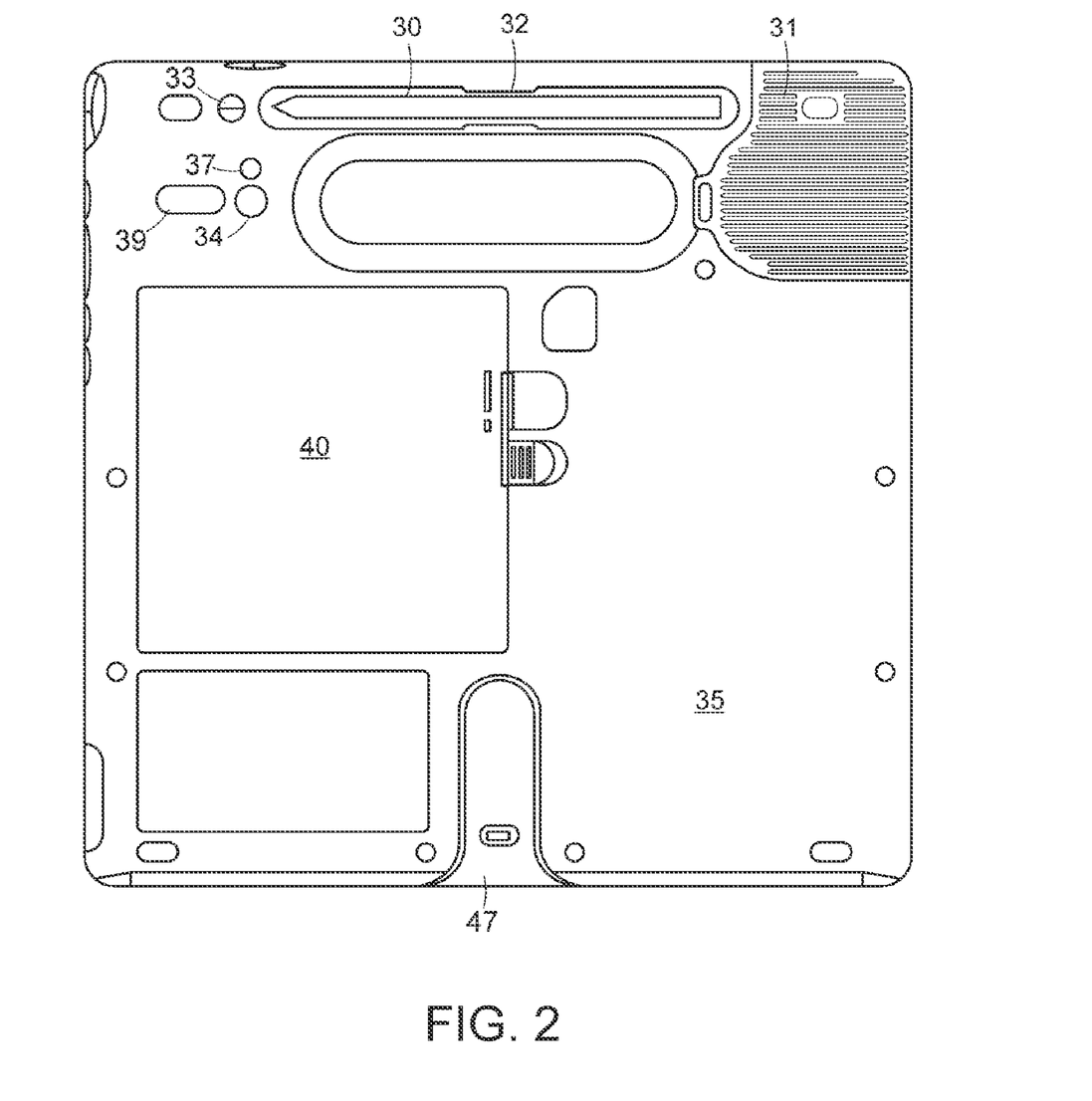
Figure 6:
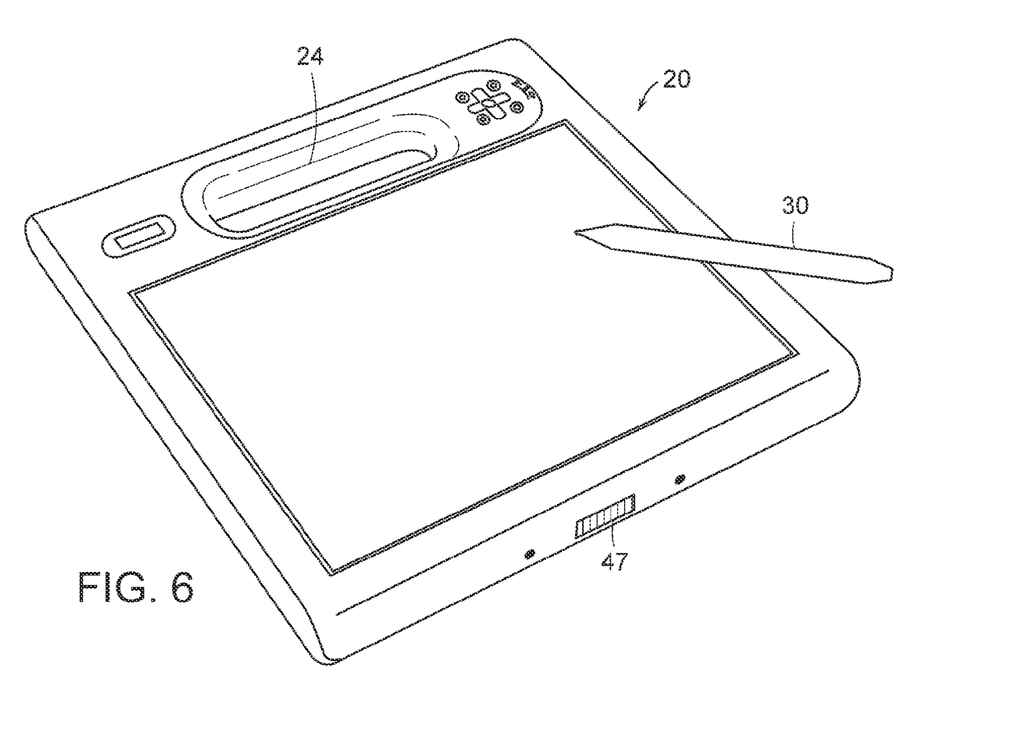
FIG. 6 is a plan view of a portable computer and stylus.

Continuing with the drawings, FIG. 2 is rear view of PC 20 (FIG. 1a). Continuing with the positive ergonomic features of a PC 20, most of the back of the device is covered by a relatively soft elastomer 22. Again, the elastomer may be Empilon, Santoprene or a similar low durometer polymer that is resistant to cleaning solutions and solvents. FIG. 2 also shows recess 32 within the handle portion of PC 20 that may be used to store stylus 30. Instead if using a keyboard or mouse to receive user input, the portable computer user may interact with the computer using the pen-type stylus 30. Stylus 30 may include a pressure-sensitive tip, a function button, and an eraser. Camera lens 34 is also location on the back of PC 20, allowing the PC to be used as a digital camera (as shown in FIG. 6).

As noted above, the portable computer may include other input/output devices and subsystems, such as a camera, a shock dection system, a specker, and a docking connector. The camera enables a user to take pictures and save then to the hard disk drive. Camera lens 34 may be on the back of the computer, and may include light 37 to illuminate the subject of a picture. The camera may produce pictures in BMP format, JPEG format, or a similar format. Two liquid-resistant microphones, as shown in FIG. 1a, may allow a user to record audio, dictate notes, and use voice commands without the need for an external microphone. The computer may also include sealed speaker 39 that can be used for audio warnings or confirmation, dictation, video playback, or other multimedia applications. Docking connector 47 may function to attach the portable computer to a docking station to connect a monitor, keyboard, mouse, or other external USB devices to the computer.

Figure 3:
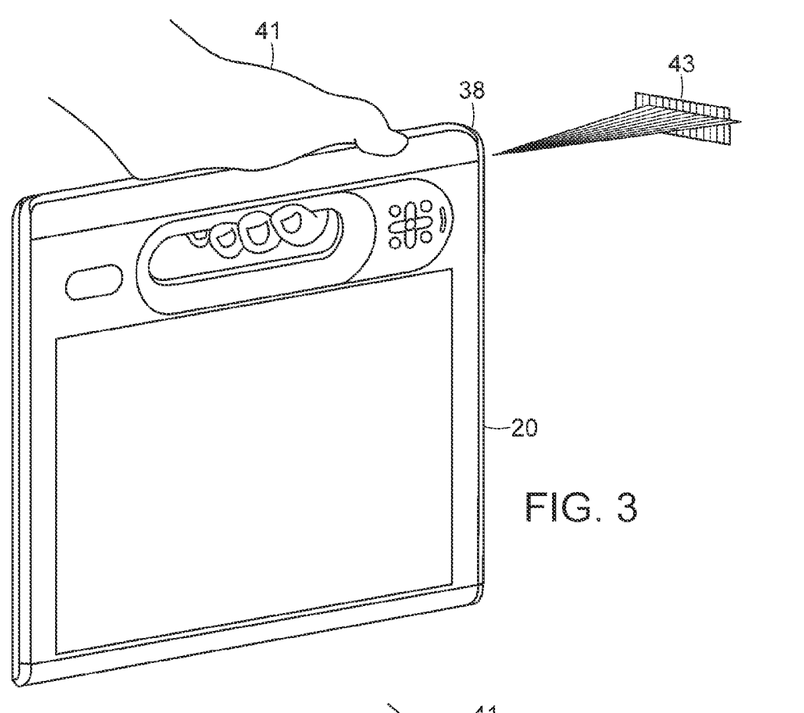
Figure 4:
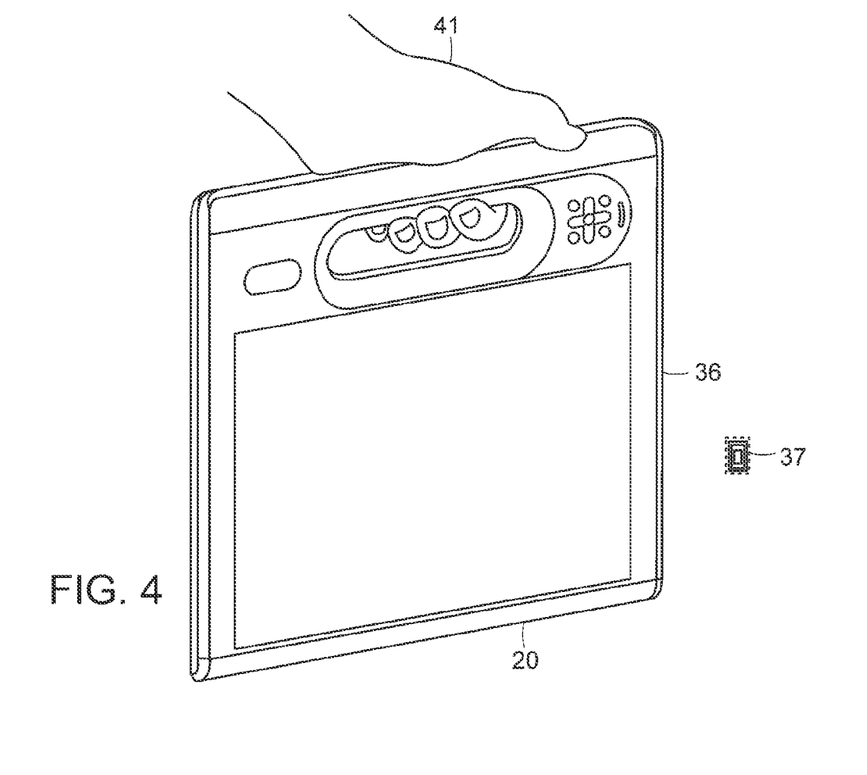

FIG. 3 illustrates how the location of the bar code scanner button in an embodiment allows a user to aim and operate bar code scanner 38 while easily supporting PC 20 using one hand. Here, the hand of user 41 is supporting PC 20, while positioning and operating bar code scanner 38 to scan bar code 43. The arrangement of the bar code scanner button, along the top of the handle of PC 20 aligns the control with the thumb of the user to facilitate one-handed operation of bar code scanner 38. FIG. 4 illustrates similar features with respect to RFID reader 36. Again, the location of the RFID reader button allows a user to aim and operate RFID reader 36 while easily supporting PC 20 with one hand. The ergonomic arrangement of the RFID reader button aligns the thumb of the user with the button so that the user can position and operate RFID reader 36 while using their free hand to accomplish other tasks.

Figure 5:
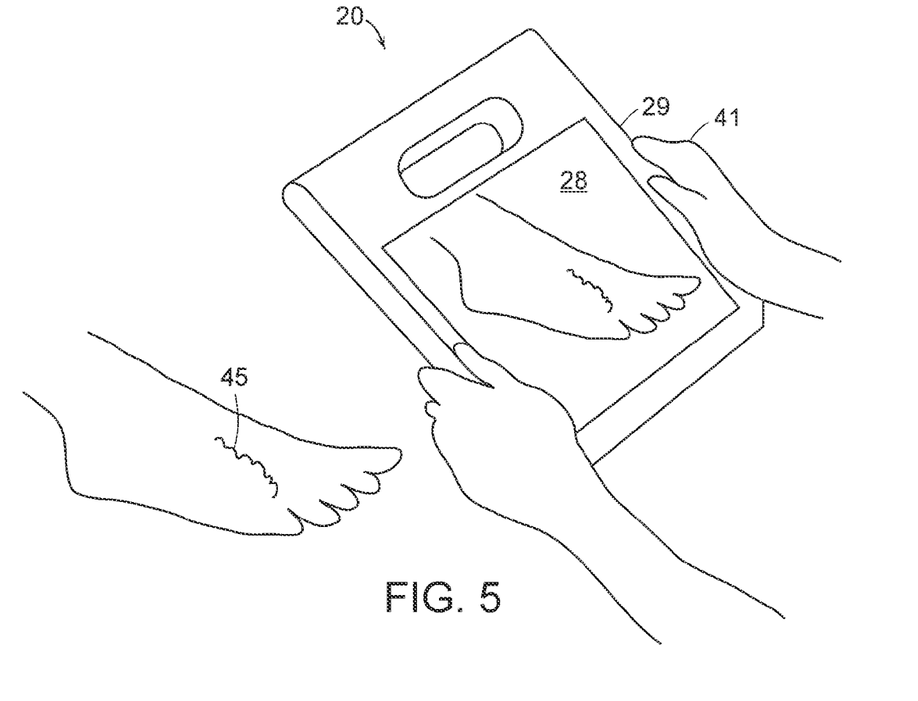

FIG. 5 shows a clinical worker using the computer to create photographic documentation of patient's wound 45. Here, the worker captures an image of patient's wound 45 by using the camera button (shown in FIG. 1c) to activate and control the camera. LCD 28 may function as a viewfinder to view the image in front of the camera lens (FIG. 2), and the camera light (FIG. 2) may illuminate the subject so the user may see a detailed representation of the photographic evidence they are creating in real time.

FIG. 6 shows PC 20 and stylus 30 that can be used as an input device for PC 20. By using a digitizer and the pen shaped stylus, a user may complete forms and take notes on the LCD screen as if it were a pad of paper. FIG. 6 also shows a pinless docking connector 47 that allows the computer to be connected to a docking station without the need for a traditional male or female docking connector. Pinless connector 47 comprises a flat surface that is easy to clean and disinfect as compared to a traditional docking connector that contains either pins or recesses that would make the connector very difficult to wipe clean.

The aforementioned stylus may be used to input data to the computer, to navigate the operating system, and to enter text by writing on the display. The stylus may feel more natural to the user than a mouse, and can be used while the user is standing or walking. An input panel GUI that allows a user to select letters from a virtual keyboard using the stylus may also be used instead of a keyboard to enter text on the portable computer without the need for an actual keyboard. Input from the stylus may be received via a digitizer positioned behind the display screen that detects the actions of the stylus. For example, the computer may include a high resolution 10.4 inch RF inductive digitizer, or a digitizer with similar functionality, mounted underneath the LCD that is configured to work with Microsoft Windows Vista™ or a similar operating system. The digitizer may enable the instant transcription of a user's notes by using text recognition software, eliminating the need for subsequent manual transcription. The computer may also be equipped to work with Bluetooth devices or devices that use similar wireless communications protocols, including Wi-Fi and WWAN networks and devices. Accordingly, the device may receive input from wireless data acquisition devices, such as stethoscopes, blood pressure monitors, thermometers, and similar devices to acquire data. This input may be instantly analyzed by a user or transmitted to a network to so that it may be accessed and stored in a central network location.

The computer may also include several types of wireless connectivity, including WWAN, Wi-Fi, and Bluetooth. Integrated Wi-Fi (802.11a/b/g) may be used to connect to the Internet, other networks, and other computers wirelessly from various locations, including many schools, hospitals, clinics, airports, hotels, or any location that offers a wireless access point. An integrated Bluetooth adapter may enable other Bluetooth enabled peripheral devices, such as computers, mice, keyboards, and PDAs, to connect to the computer via a short-range wireless connection.

The computer's unique set of integrated input devices may assist users to create documentation, administer medication, and manage work flow. Users may also use the computer to access and update patient data, scheduling information, and/or similar data at any time. This may have the effect of eliminating wasteful double documentation, increasing the accuracy of reported information, and in turn decreasing the potential for errors in transcription of information and medication administration. In short, the computer may greatly improve a healthcare worker's ability to correctly administer medication and treatment to patients.

The computer may be mounted in a docking station by connecting it with the docking connector referenced in FIG. 1a. The docking station may contain two recesses. The first recess may be used to dock PC 20, while the second recess may store and charge a second battery. Charging can occur via pinless mating connectors or through magnetic energy, thus avoiding any protruding pins or cavities where dirt, bacteria, or other contaminants can accumulate. The docking station may be used to store the computer in an upright position at which the monitor is easily readable, while charging the battery of the computer and equipping it with peripheral devices that are generally associated with desktop computers. The docking station may also include a video output connector, such as VGA, HDMI, DVI, and S-Video connectors and a USB hub. The USB hub may enable the computer to connect to any USB enabled device and an Ethernet connection to equip the computer with a wired connection to a LAN without the need for a dedicated connector on the PC. By routing all wired peripheral device connections through the docking station, the computer itself may remain free of complex connector recesses, making it easier to clean and more resistant to contamination.

When the portable computer is either not in use or used in a stationary working environment, such as an office, it may be placed in a docking station. This may be the ideal way to recharge the battery of the computer while also equipping the PC with the functionality of a desktop computer. Depending on whether the dock is being used for storage or to support the computer at a viewable angle, the docking station may contain a pivot so that the computer may rest at a variety of angles. For instance, at a first angle, the dock may support the computer in an upright position when resting on a horizontal surface, so that it is easily viewable by a seated or standing user. At a second angle, the dock may support the computer at an angle that is parallel, or nearly parallel, to the surface on which the dock rests or is mounted so that the profile of the computer relative to the surface is minimized. The docking station may also have one or more intermediate positions to accommodate scenarios with differing geometry (e.g. a standing user or a short desktop viewing angle). In some cases, it may be desirable to mount one or more docking stations to a wall so that multiple computers may be stored and charged without occupying table or desk space. In order to mount the docking station to a wall in a secure position, it should store the computer at an angle that does not cause the computer to protrude too far from the wall or sit in an unstable position. For example, in one embodiment, the docking station may be wall mounted and configurable to hold a PC so that when docked, it will protrude no more than 4" from the wall. The docking station may also have an indicator, such as an LED light, to indicate whether or not a battery is fully charged and may also contain a USB hub as well as other input/output connectors.

In order to prevent contamination, it is important for the computer to be relatively well sealed. As such, any seams, joints, or openings of the computer may be sealed so that the computer will conform to IP Code 54, as defined in international standard IEC 60529 which is herein incorporated by reference, as well as less stringent IP Code 53. To conform to IP Code 54, a device must resist water ingress when exposed to splashing water and also resist particulate infiltration when exposed to the conditions of a dusty environment. This sealing may be accomplished by including a compressible seal, such as an O-ring or similar sealing mechanism between any joints or seams in the body of the device. The body of the computer may comprise multiple parts that are fastened together with a compressible gasket between them to resist penetration by liquids, moisture, and even contaminated air. The housing of the battery may be similarly designed to include a seal so that only the external surface of the computer and battery may need to be wiped clean to effectively sanitize the computer. Further, the thumb controls of the computer may be snap dome sensors, capacitive touch sensors, or a similar sensor that does not require an opening in the surface of the computer. As such, even the controls of the computer may comprise a smooth surface that is easy to clean and resistant to contamination from dirt, germs, and/or biological fluids.

Figure 7:
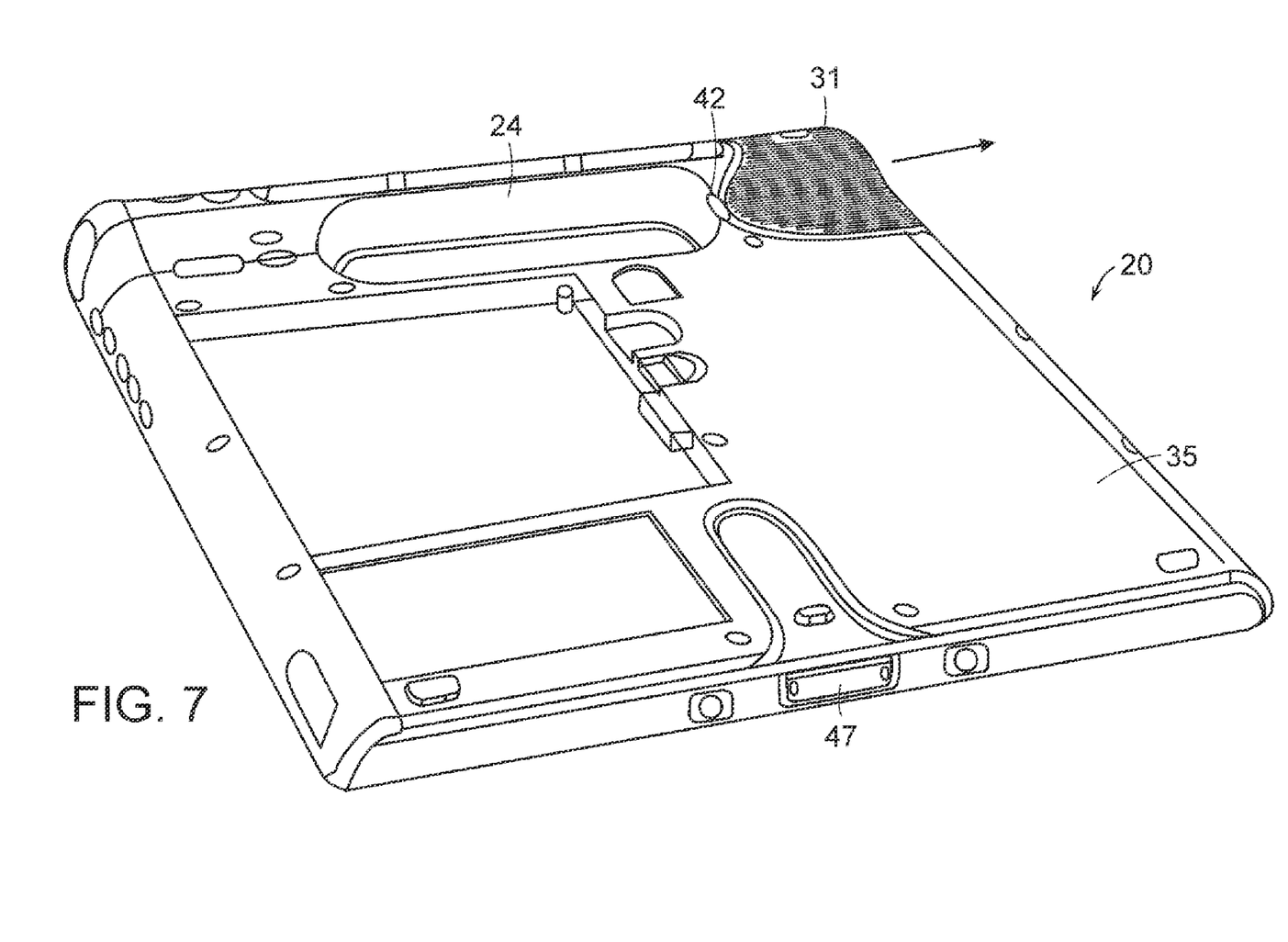
FIG. 7 is a plan view showing the rear and bottom surfaces of a portable computer.

Turning to FIG. 7, fan cover 31 may be removed and cleaned if it becomes soiled. To clean the fan cover, a user may press the fan cover release latch 42 and slide fan cover 31 away from sealed rear cover 35 of PC 20 to remove it. The user may then clean fan cover 31 according to the guidelines of their organization, and slide fan cover 31 back onto PC 20 until it snaps into place after it has been cleaned and dried. The fingerprint reader (shown in FIG. 1*c*) may also be wiped clean.

In addition to the various integrated devices outlined above, including the RFID reader, bar code scanner, and digital camera, the tablet computer may also have an abundant set of input and output devices. Of note, the computer may transmit and receive sound data via a wireless communications controller in conjunction with an audio subsystem that includes a speaker system. The PC may also have wireless communications capability to transmit gathered patient information to a central network location so that patient files can be updated instantaneously. In the healthcare environment, this means that up to the minute information consisting of pictures, vital sign measurements, and other patient data may be readily available. In other working environments, many of the same tools may be used to track work flow, delivery, and manufacturing statistics.

The personal computer may employ a high level operating system, such as Microsoft Windows Vista™, that includes ink-to-text and word recognition, voice recognition, and improved security to help defend against viruses, worms, and other threats. The higher level operating system may also allow the computer to run more sophisticated software applications. The computer may also include a customizable control panel or graphical user interface (GUI) may allow a user to enable or disable Bluetooth, WWAN, and Wi-Fi, calibrate the digitizer, or check the remaining battery power.

To store data, the computer may contain at least one hard disk drive (HDD), as specified by a design engineer. In some embodiments, the computer may employ a solid state memory, or solid state drive (SSD) instead of or in addition to an HDD. Using a SSD that contains no moving parts may help the computer to withstand impact because moving parts are more likely to sustain damage as a result of impact. In order to protect a HDD with moving parts, the computer may employ a shock detection system. The shock detection system may detect shocks, extreme vibrations, and falls. When a shock, extreme vibration, or a fall is detected, the shock detection system may park the HDD heads away from the disk, which can prevent HDD failures and data loss. The shock detection system may be achieved by considering input from an accelerometer that is coupled to the device. An accelerometer may be a micro-electromechanical (MEMS) device, or MEMS accelerometer, that contains at least one accelerometer or inclinometer. The accelerometer may monitor changes in acceleration along three major axes so that it may detect almost any motion sustained by a device. Accelerometers vary in the sensitivity of their target applications in that they are able to measure magnitude of acceleration on a scale of 0-1.5 g for higher resolution applications and 0-6 g (or more) in lower resolution applications. Here, a higher resolution accelerometer, such as a 1.5 g accelerometer may be used.

An exemplary accelerometer may contain a packaged sensor element and is designed to have a customizable sensitivity level in terms of the amount of motion or change in position that is required to cause the device to generate an interrupt signal. The interrupt signal may be generated for a change in acceleration on any axis above a predetermined threshold value when the device is programmed to detect motion, and may be generated for a change in acceleration on all three axes below a threshold value with the device is programmed to detect a freefall. Generally, the sensor element may function on the principle of differential capacitance by including a displaceable silicon structure that is displaced when the sensor is subject to acceleration. The displacement of the silicon structure may generate a change in capacitance when it undergoes acceleration, and the change in capacitance can be used to generate an output voltage that corresponds to the experienced acceleration. By taking measurements as often as one hundred times per second, an accelerometer can detect even the slightest angular or linear movements. In practice, accelerometers have been observed to detect a free-fall before a device has fallen three inches. As such, the accelerometer may help to protect the HDD from damage during a fall by immediately detecting a freefall and generating an interrupt signal that parks the heads of the HDD so that it will be less likely to sustain damage.

Figure 8:
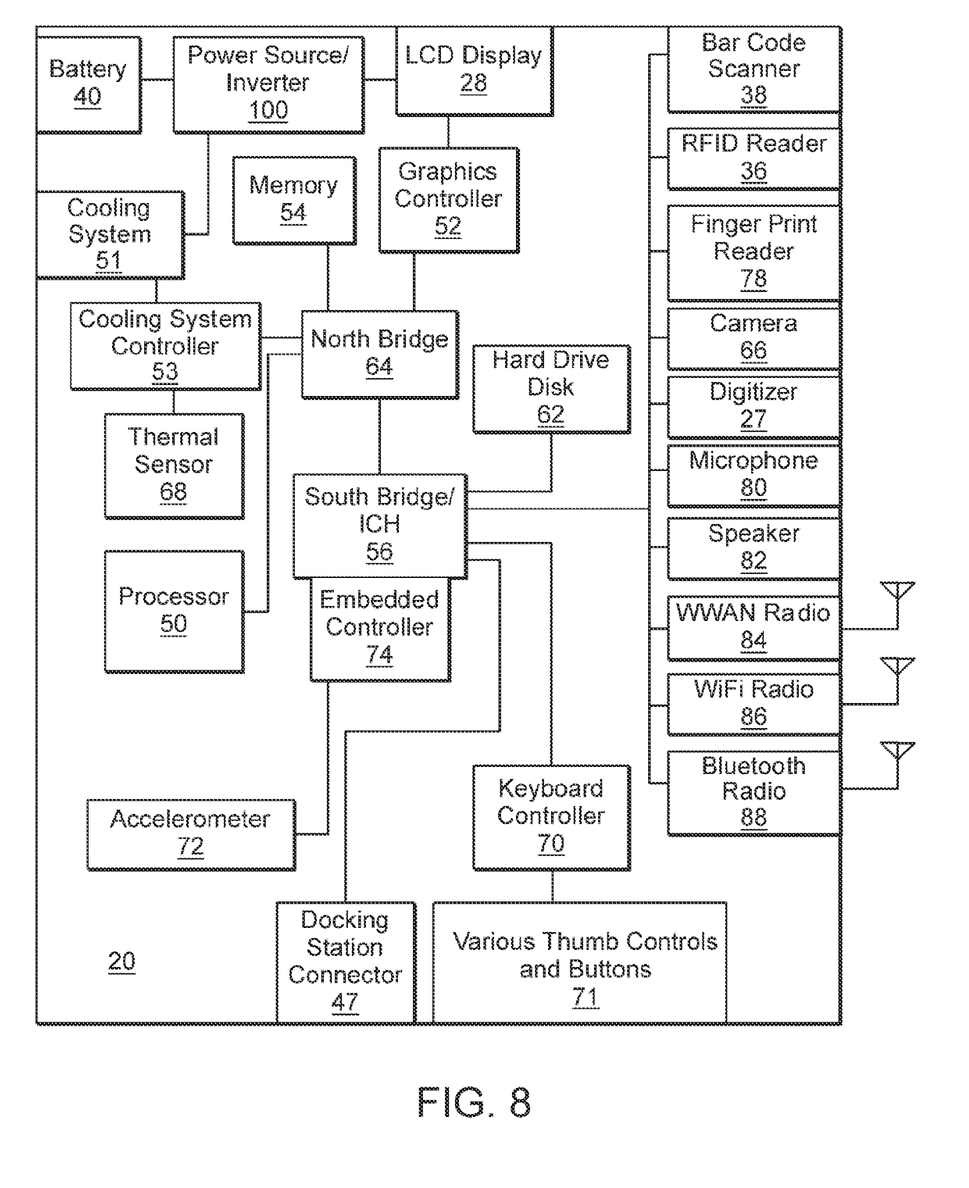
FIG. 8 is a block diagram of at least a portion of a representative architecture for a portable computer that is optimized for use in a clinical environment.

FIG. 8 is a block diagram showing a representative architecture of a portion of PC 20 that is optimized to function in a clinical environment. PC 20 contains processor 50 that is connected to north bridge 64 and input/output controller hub (ICH) 56 or south bridge. Here, the north bridge may connect memory 54 and graphics controller 52 which may operate LCD 28. To power LCD 28, a power source or inverter 100 may be included and connected to battery 40. Power source 100 may be a significant source of heat, and as such may be thermally coupled to cooling system 51. Cooling system 51 may be controlled by cooling system controller 53, which may receive input from one or more thermal sensors 68. ICH 56 may connect a multitude of input/output devices, which are discussed in more detail below, to PC 20. Accelerometer 72 and thermal sensor(s) 68 are connected via embedded controller 74. ICH 56 may extend USB, Ethernet, or similar input/output (I/O) connectors to docking station connector 47. Also via ICH 56, keyboard controller 70 may receive user input via the various thumb controls/buttons 71. Here, the computer may be somewhat adaptable and customizable because each sensor may be assigned a unique identifier by a controller, such as keyboard controller 70. The controller may use the identifier to communicate user input to the processor. Particular sensors, or thumb controls, may be associated with particular features of the computer, such as the operation of the camera, RFID reader, or bar code scanner, while other sensors may be associable with the same or different features as specified by a user.

PC 20 may also have HDD 62 and/or SSD that is connected via ICH 56. To gather data, ICH 56 may connect bar code scanner 38, RFID reader 36, camera 66, finger print scanner 78, digitizer 27, and microphone array 80. To output sound to a user, PC 20 may also have speaker(s) 82 that are connected through the ICH. PC 20 may also house a variety of radios that are also connected via ICH 56. A WWAN transceiver and antenna 84 may connect PC 20 to a wireless broadband network; a WiFi transceiver and antenna 86 may connect PC 20 to a wireless local area network; and a Bluetooth transceiver and antenna 88 may enable the computer to communicate with Bluetooth enabled devices. Because the PC may contain multiple radios, it may be necessary to selectively activate and deactivate particular radios, such as the WWAN and WiFi radios, so that they do not transmit simultaneously. The remaining radios may be selectively activated or deactivated based on user input and automated processes, such as power management settings.

A mapping driver may also be included to map computer controls to the various additional integrated devices, such as the camera, RFID reader, and bar code scanner in a way that is independent of the operating system. This will allow the software used with the integrated devices to communicate with the thumb controls and/or associated indicators that may be controlled by the keyboard controller. The mapping driver may also function to provide an interface between an operating system, such as Microsoft Windows Vista™, and/or the BIOS of the computer. The mapping driver may also communicate with drivers associated with the various integrated devices to obtain control settings such as input signals and output indicators. The driver may interface with operating system's registry to determine configuration information associated with the various integrated devices and associated inputs and outputs. Additionally, the driver may interface with the BIOS of the computer and thereby implement control methods based on input from thermal sensors within the computer as noted above when the higher level operating system is not functional. Additionally, a user interface, such as the Motion Computing Dashboard Utility, may be incorporated to control the integrated devices as well as other features of the computer.

Since the computer may be sealed, it may be difficult to cool because a completely sealed cooling system can only cool through passive means. In other words, sealing the computer forecloses the option of cooling it by circulating cooler air from the ambient environment through the computer. When more heat is generated than can be passively cooled, the computer may either expose a user to an excessively hot surface or limit heat generation by limiting processing power. Limiting processing power, or throttling the processor, may render the computer less effective, but may be necessary to prevent the computer from sustaining damage caused by excessive heating.

As performance and processing power of the computer are improved, for example, by incorporating faster processors, the computer may generate heat at even higher rates. Since the passive cooling system may offset the benefit of a faster processor, the limitations associated with passively cooling the computer may become a significant hindrance. Still, it is noted that in some circumstances, scaling back the performance of the processor to limit heat generation may be a viable mode of cooling. To this end, many processors are equipped with built-in thermal sensors. These sensors and other thermal sensors installed in the computer may monitor thermal conditions at key points inside the computer. In a passively cooled system, these sensors may generate interrupt signals at particular temperatures to initiate processor limitations, automatic saving of sensitive system data, and even an emergency shut-down when a critical temperature is reached. Additionally, particular subsystems, such as the backlight of the LCD, can be powered down to conserve power and limit heat generation.

To maximize passive cooling capacity, the computer may have a chassis and one or more exterior plates that are designed to conduct heat away from the computer and dissipate it into the surrounding environment. These conductive elements may be thermally coupled to the portions of the computer that generate the most heat, such as the processor and power supply, by using thermal greases, heat pipes, heat spreading materials such as GraphTech's Spreadershield, a graphite based heat spreading material, and similar conductive materials. To maximize the ability of the computer to dissipate heat, the frame and body of the computer may be made from a thermally conductive material, such as a magnesium-alloy. While this type of construction may allow portions of the computer to become quite hot, a user can be insulated from excessive heat by the elastomer overmolding (or similar insulating layer). For instance, while internal components of the computer may reach temperatures at or near 65° C., the external surface of the computer may remain below 55° C.

While it may be desirable to maximize the extent to which passive cooling is used, it is unlikely that a passive cooling system will adequately cool the PC if it operates at a reasonable processing capacity for an extended period of time. As such, it may be desirable to seal as much of the computer as possible and incorporate a partially sealed active cooling system that includes a radiator and fan assembly in a portion of the device that is outside of the sealed cover of the PC. In other words, while substantially all of the computer may be sealed, thermally conductive elements, such as heat pipes, may be used to conduct heat to an unsealed location where it can be actively dissipated.

Figure 9:
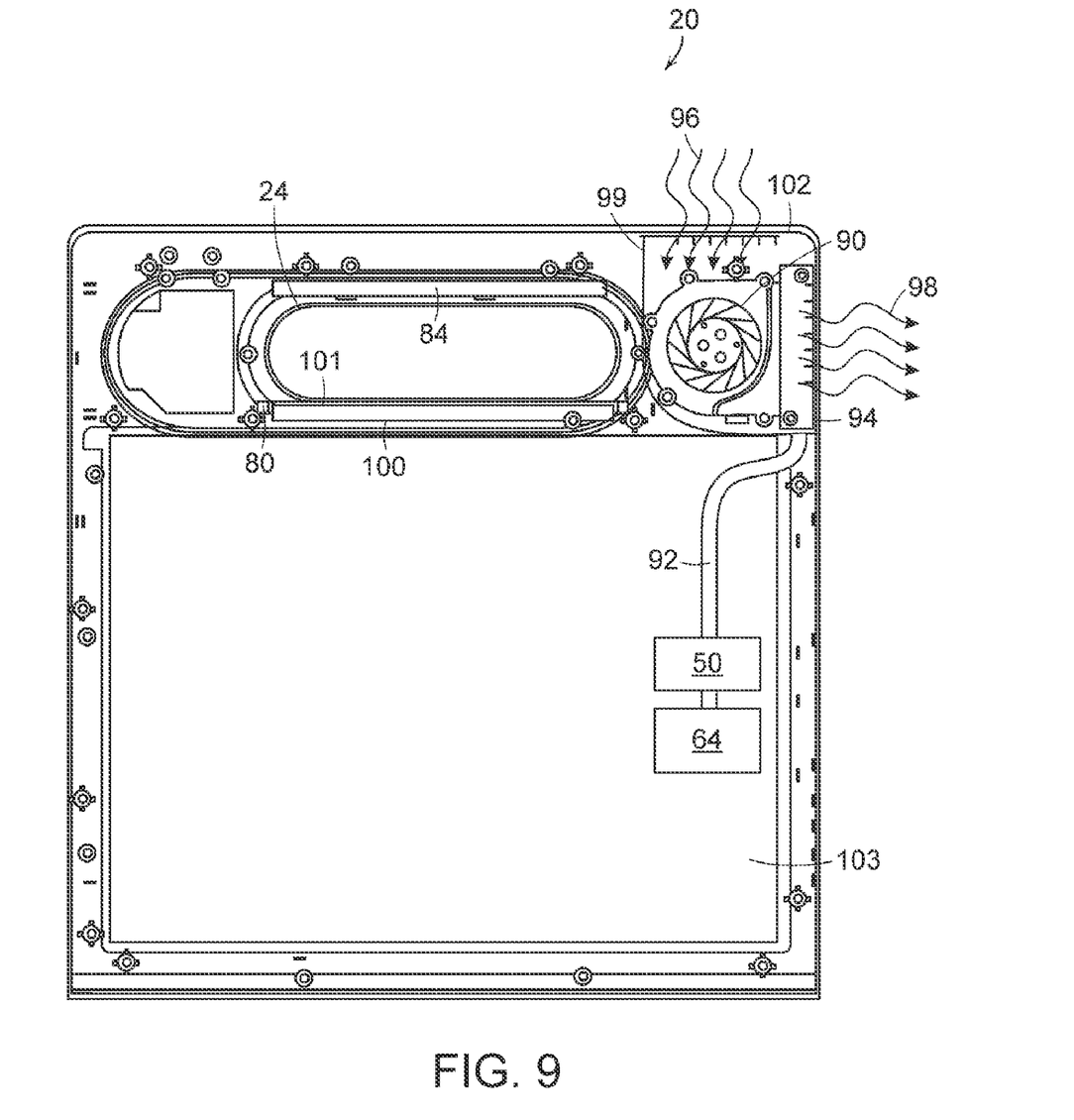
FIG. 9 is a rear perspective view of a portable computer with the rear covers removed to show at least a portion of internal components of the portable computer.

FIG. 9 shows a rear view of PC 20 with the rear cover removed. Here, the locations of active cooling components can be seen along with the other components located near handle 24. Below handle 24, PC 20 houses microphones 80 that are connected via microphone cable 101, along with electrical power source 100 that may power the backlight of the LCD. In this embodiment, the power source is a power inverter that may convert power received from the DC power source of the device to AC power that is supplied to the backlight of the LCD. Above handle 24, the computer houses WWAN radio 84. To the right of handle 24, the computer houses components of the partially sealed active cooling system. While the bulk of the components of PC 20 are sealed within sealed area 103 of PC 20, an active cooling system may be necessary to adequately cool PC 20. Here, heat pipes 92 may protrude across boundary 99 between sealed area 103 and unsealed area 102 that houses fan 90 and radiator 94. Heat pipes 92 may draw heat to the radiator from heat producing parts of PC 20, such as the processor and power supply. Because the heat pipes must follow a complex path that cannot be easily formed from flat heat pipe material, heat pipes 92 may be formed from round heat pipe material and flattened on the ends to increase thermal conductivity and contact areas at locations where heat pipes 92 absorb or dissipate heat. In unsealed area 102 of PC 20, heat pipes 92 may be coupled to radiator 94. Here, fan 90 may circulate cooler air 96 from the ambient environment across radiator 94 so that heat from the radiator may be dissipated into the air that is then discharged as warmer air 98. While this portion of PC 20 is open to the ambient environment, it should still be configured so that it can be sprayed with a disinfectant or cleaning material and wiped clean to the extent possible. Accordingly, it is desirable to select a fan that is easily replaceable and tolerant to moisture.

In sum, a portable computer is disclosed that is optimized and equipped with a robust feature set that makes it ideal for use in medical environments and other challenging work environments. The portable computer is highly ergonomic, impact resistant, and resistant to moisture penetration and contamination from airborne contaminants. The device is also easily cleaned by virtue of its sealed design that makes it resistant to cleaning agents that may be used to remove dirt or kill germs and bacteria. It will be appreciated to those skilled in the art having the benefit of this disclosure that this invention is believed to provide a multi-purpose portable computer that has improved utility in the healthcare as well as other industries. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit if this description of the invention. Changes may be made in the elements described herein without departing from the spirit and scope of the invention as described in the following claims.

What is claimed is:

1. A portable computer, comprising:
   at least two radios, wherein a first radio is configured to transmit and receive data at a first time, and wherein a second radio is configured to transmit and receive data at a second time;
   at least two data capture devices, wherein a first data capture device is configured to gather data at a third time, wherein a second data capture device is configured to gather data at a fourth time, and wherein one of the at least two data capture devices comprises a light source that is controlled independently of the one of the at least two data capture devices to illuminate a subject;
   an accelerometer configured to measure acceleration of the portable computer along three axes and to generate an interrupt signal when the acceleration measured along at least one of the three axes exceeds a pre-selected magnitude; and
   a hard disk drive configured to cease movement upon receiving the interrupt signal from the accelerometer.

2. The portable computer of claim 1, wherein the first, second, third, and fourth times are at least partially mutually inclusive of each other.

3. The portable computer of claim 1, wherein the first, second, third, and fourth times are mutually exclusive of each other.

4. The portable computer of claim 1, wherein the at least two radios are selected from a group consisting of a WWAN radio, a Bluetooth radio, a WiFi radio, and an RFID reader.

5. The portable computer of claim 4, wherein the at least two data capture devices are selected from a group consisting of a bar code scanner, a camera, and a fingerprint scanner.

6. The portable computer of claim 1, wherein the at least two data capture devices are selected from a group consisting of a bar code scanner, a camera, and a fingerprint scanner.

7. The portable computer of claim 1, further comprising a solid state memory having no moving parts.

8. The portable computer of claim 1, further comprising a display screen having a protective layer that offers a firm writing surface and minimizes glare, and a digitizer panel that enables user input to be entered via a stylus.

9. The portable computer of claim 1, further comprising at least one microphone that enables a user to record audio, dictate notes and issue voice commands used to operate the portable computer.

10. The portable computer of claim 1, further comprising a plurality of control buttons for controlling operation of the portable computer.

11. The portable computer of claim 10, wherein the plurality of control buttons comprise:
    a function button configured to activate secondary functions for the control buttons;
    a dashboard button that calls a control panel type graphical user interface;
    a first customizable button and a second customizable button to which a user assigns programmable functions; and
    a directional pad having up, down, left and right scroll functionality.

12. The portable computer of claim 10, wherein the plurality of control buttons comprise at least two buttons configured for operating the at least two data capture devices.

13. The portable computer of claim 1, wherein the light source is independently controlled by a user of the portable computer via a control button or through a control panel utility of the portable computer.

14. An electronic device, comprising:
  an accelerometer configured to measure acceleration of the electronic device along three axes and to generate an interrupt signal when the acceleration measured along at least one of the axes exceeds a pre-selected magnitude;
  a hard disk drive configured to cease movement upon receiving the interrupt signal from the accelerometer;
  at least two antennas internal to the electronic device; and
  at least two data capture devices internal to the electronic device, wherein one of the at least two data capture devices comprises an illumination source that is controlled independently of the one of the at least two data capture devices to illuminate a subject.

15. The electronic device of claim 14, wherein the at least two antennas are configured to operate according to a protocol selected from a group consisting of WWAN radio, Bluetooth, WiFi radio, ISO/IEC 14443A/B, ISO/IEC 15693, and ISO/IEC 18000-3, and wherein the at least two data capture devices are selected from a group consisting of a bar code scanner, a camera, and a fingerprint scanner.

16. The electronic device of claim 14, wherein the illumination source is independently controlled by a user of the electronic device via a control button or through a control panel utility of the electronic device.

* * * * *